(12) United States Patent
Li et al.

(10) Patent No.: US 11,460,020 B2
(45) Date of Patent: Oct. 4, 2022

(54) MICRO-DELIVERY DEVICE (71) Applicant: MicroMED Co., Ltd., Taipei (TW)

(72) Inventors: Po-Ying Li, Taipei (TW); Tsung-Chieh Cheng, Kaohsiung (TW)

(73) Assignee: MICROMED CO., LTD., Taipei (TW)

(*) Notice: Subject to any disclaimer, the term of this patent is extended or adjusted under 35 U.S.C. 154(b) by 229 days.

(21) Appl. No.: 16/793,143

(22) Filed: Feb. 18, 2020

(65) Prior Publication Data
US 2020/0263679 A1 Aug. 20, 2020

Related U.S. Application Data (60) Provisional application No. 62/807,538, filed on Feb. 19, 2019.

(51) Int. Cl.
| | | |
|---|---|---|
| F04B 19/00 | (2006.01) | |
| F04B 43/04 | (2006.01) | |
| F16K 99/00 | (2006.01) | |
| B65D 83/00 | (2006.01) | |
| A61M 5/145 | (2006.01) | |
| A61M 5/142 | (2006.01) | |

(52) U.S. Cl.
CPC ........... *F04B 43/043* (2013.01); *A61M 5/142* (2013.01); *A61M 5/14526* (2013.01); *A61M 5/14593* (2013.01); *B65D 83/00* (2013.01); *B65D 83/0055* (2013.01); *F04B 19/006* (2013.01); *F16K 99/0015* (2013.01); *A61M 2005/14204* (2013.01); *A61M 2205/8231* (2013.01)

(58) Field of Classification Search
CPC ...... F04B 43/043; F04B 19/006; B65D 83/00; B65D 83/0055; F16K 99/0015; A61M 5/142; A61M 5/14526; A61M 5/14593; A61M 2005/14204; A61M 2205/8231
See application file for complete search history.

(56) References Cited

U.S. PATENT DOCUMENTS

| | | | |
|---|---|---|---|
| 11,058,814 B2* | 7/2021 | Li | A61M 5/14276 |
| 2007/0159031 A1* | 7/2007 | Yokoyama | H02N 11/006 310/31 |
| 2009/0093772 A1* | 4/2009 | Genosar | A61M 5/14244 604/246 |
| 2011/0134349 A1* | 6/2011 | Wu | G02F 1/13781 349/34 |
| 2011/0270188 A1* | 11/2011 | Caffey | A61M 5/14593 604/151 |
| 2013/0178826 A1* | 7/2013 | Li | A61M 5/155 604/506 |
| 2013/0184640 A1* | 7/2013 | Li | A61M 5/14526 604/67 |
| 2014/0008555 A1 | 3/2014 | Li et al. | |

(Continued)

*Primary Examiner* — Frederick C Nicolas
(74) *Attorney, Agent, or Firm* — Birch, Stewart, Kolasch & Birch, LLP (57) ABSTRACT

A micro-delivery device includes a substrate having an upper surface; a shell disposed on the upper surface of the substrate and defining a chamber between the shell and the substrate; a planar electrode disposed on the upper surface of the substrate; a separator disposed in the chamber and dividing the chamber into an upper reservoir and a lower reservoir; and a cannula inserted in an opening of the rigid shell and in fluid communication with the upper reservoir.

20 Claims, 7 Drawing Sheets

(56) References Cited

U.S. PATENT DOCUMENTS

| | | | |
|---|---|---|---|
| 2014/0088554 A1* | 3/2014 | Li | A61M 5/14248 |
| | | | 604/506 |
| 2014/0094771 A1* | 4/2014 | Li | A61M 5/16809 |
| | | | 604/506 |
| 2014/0374245 A1* | 12/2014 | Dunn | C25B 11/04 |
| | | | 204/275.1 |
| 2018/0104408 A1 | 4/2018 | Li et al. | |
| 2020/0122173 A1* | 4/2020 | Adam | A61M 5/2466 |

* cited by examiner

MICRO-DELIVERY DEVICE

CROSS-REFERENCE

This Non-provisional application claims the priority under 35 U.S.C. § 119(a) on U.S. Patent Provisional Application No. 62/807,538 filed on Feb. 19, 2019, the entire contents of which are hereby incorporated by reference.

FIELD OF THE INVENTION

The disclosure relates to a micro-delivery device. More particularly, the disclosure relates to an electrochemical pump for a micro-delivery device.

BACKGROUND OF THE INVENTION

Conventionally, smooth microelectrode was used in the electrolysis pump product. Previously, an improvement has been developed to use electroplating microelectrode to increase surface roughness in order to increase the power efficiency for the pump. However, this production method for this electrode design cannot give repeated morphology of the electrode surface reducing the reliability for the energy performance of the pump.

Recently, minimized delivery pumps of therapeutic agents have been proposed to improve the issues in pharmaceutical industry. However, some deficiencies still waiting to be improved for conventional designs on delivery pumps of therapeutic agents. For example, low pump energy efficiency for the conventional pump electrode structure due to lower local electrical field in electrolyte and low pump energy efficiency from lower solid surface free energy.

A need therefore exists for apparatus and methods to be improved and to solve at least one of the above-mentioned pending problems.

SUMMARY OF THE INVENTION

An aspect provided herein is a micro-delivery device, comprising: a substrate having an upper surface; a shell disposed on the upper surface of the substrate and defining a chamber between the shell and the substrate; a planar electrode disposed on the upper surface of the substrate; a separator disposed in the chamber and dividing the chamber into an upper reservoir and a lower reservoir; and a cannula inserted in an opening of the rigid shell and in fluid communication with the upper reservoir; wherein at least one sharp corner is formed on the surface of the planar electrode.

In a particular embodiment, the planar electrode has a first side surface and a second side surface which is opposite to the first side surface in a cross-sectional view, and at least one sharp corner is formed on the first side surface and/or the second side surface respectively.

In a particular embodiment, the planar electrode has a first side surface and a second side surface which is opposite to the first side surface in a cross-sectional view, the planar electrode further has a top surface connecting the first side surface and the second side surface, and at least one sharp corner is formed on the top surface.

In a particular embodiment, the planar electrode further comprises a top surface and a bottom surface opposite to the top surface, and an area of the top surface is larger than an area of the bottom surface, forming a sharp corner between the side surface and the top surface from a cross-section view.

In a particular embodiment, the sharp corner has a sharp angle which has a range between 0.01-90°.

In a particular embodiment, the sharp corner has a width which has a range between 0.01-100 μm.

In a particular embodiment, the sharp corner is formed by the method of isotropic etching or anisotropic etching.

In a particular embodiment, the sharp corners are formed at and protruded from the surface in the shape of zig-zag.

In a particular embodiment, the sharp corners are formed at and protruded from the surface in the shape of tip of pyramid.

In a particular embodiment, the planar electrode is a porous electrode.

In a particular embodiment, further comprising an electronic device is electrically connected to the planar electrode.

In a particular embodiment, the planar electrode is hydrophilic and the substrate is hydrophilic.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

The following embodiments when read with the accompanying drawings are made to clearly exhibit the above-mentioned and other technical contents, features and effects of the present disclosure. Through the exposition by means of the specific embodiments, people would further understand the technical means and effects the present disclosure adopts to achieve the above-indicated objectives. Moreover, as the contents disclosed herein should be readily understood and can be implemented by a person skilled in the art, all equivalent changes or modifications which do not depart from the concept of the present disclosure should be encompassed by the appended claims.

As used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

Furthermore, the ordinals recited in the specification and the claims such as "first", "second" and so on are intended only to describe the elements claimed and imply or represent neither that the claimed elements have any proceeding ordinals, nor that sequence between one claimed element and another claimed element or between steps of a manufacturing method. The use of these ordinals is merely to differentiate one claimed element having a certain designation from another claimed element having the same designation.

Furthermore, the terms recited herein such as "on", "above", "over" or the like are intended not only direct contact with the other component, e.g. a substrate, but also intended indirect contact with the other component, e.g. a substrate.

Embodiment 1

Figure 1:
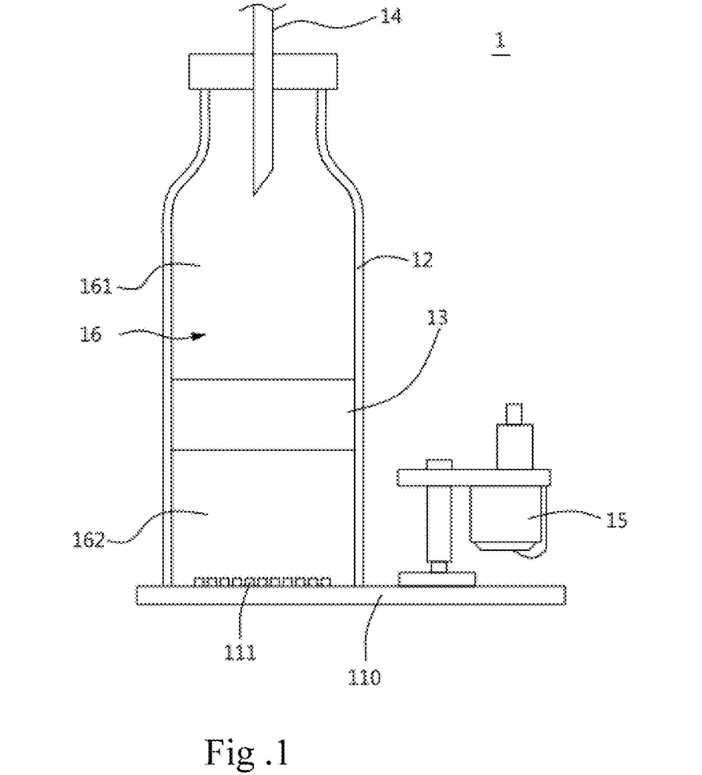
FIG. 1 is a schematic cross-section view of a delivery device according to embodiment 1 of the disclosure.

Please refer to FIG. 1, which is a cross-sectional view of a delivery device according to embodiment 1 of the disclosure. As shown in FIG. 1, the delivery device 1 which comprises an substrate 110, a rigid shell 12, a separator 13, a cannula 14 and an electronic device 15.

A planar electrode 111 and the rigid shell 12 are disposed on the upper surface of the substrate 110, and a chamber 16 defined by the rigid shell 12 and the substrate 111. The separator 13 is configured within the chamber 16 to divide the chamber into an upper reservoir 161 and a lower reservoir 162. A therapeutic agent can be filled in the upper reservoir 161. A liquid reagent for electrolysis can be filled in the lower reservoir 162. The cannula 14 is inserted in an opening of the rigid shell 12 and is in fluid communication with the upper reservoir 161. The electronic device 15 is electrically connected to the planar electrode 111 and provides electric power to the planar electrode 111. In the present embodiment, the separator is a diaphragm. The substrate 110, the planar electrode 111, the cannula 14, the chamber 16, and the separator 13 together compose an electrochemical pump of the present invention, which is used to delivering the drug. Furthermore, the separator 13 is made of rubber plunger, which is used as a stopper.

Embodiment 2

Figure 2:
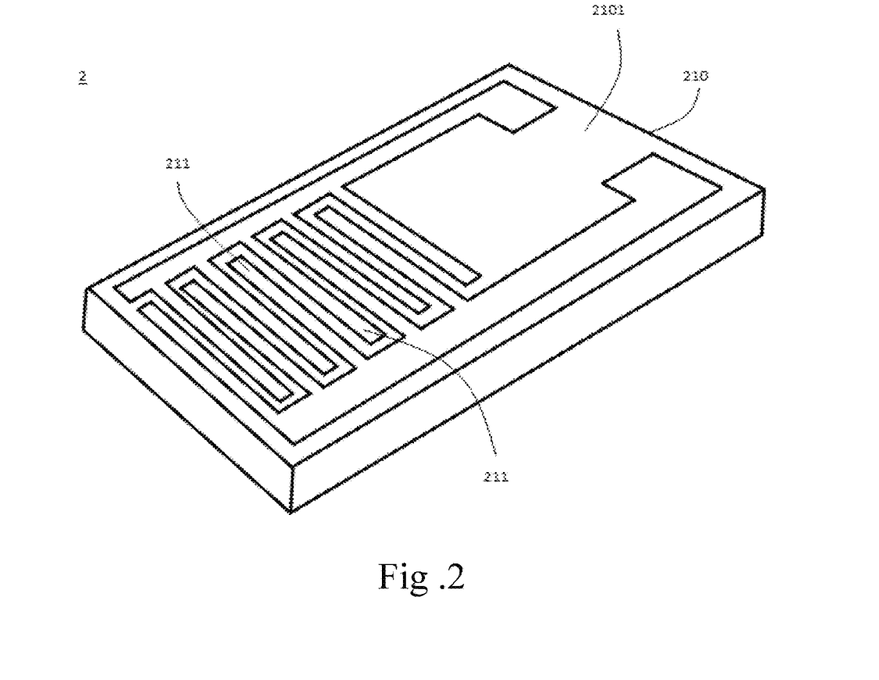
FIG. 2 is a three-dimensional view of an electrochemical pump according to embodiment 2 of the disclosure.

Please refer to FIG. 2, which is a three-dimensional view of an electrochemical pump according to embodiment 2 of the disclosure. As shown in FIG. 2, the electrochemical pump 2 comprises a substrate 210 and at least one planar electrode 211 (for example, anode and cathode electrodes).

The substrate 210 has an upper surface 2101. Additionally, the substrate 210 can be, but not limited to, made of bio-compatible materials. In the present embodiment, the substrate 210 is made of glass.

The planar electrode 211 is disposed on the upper surface 2101 of the substrate 210.

Embodiment 3-1

Figure 3:
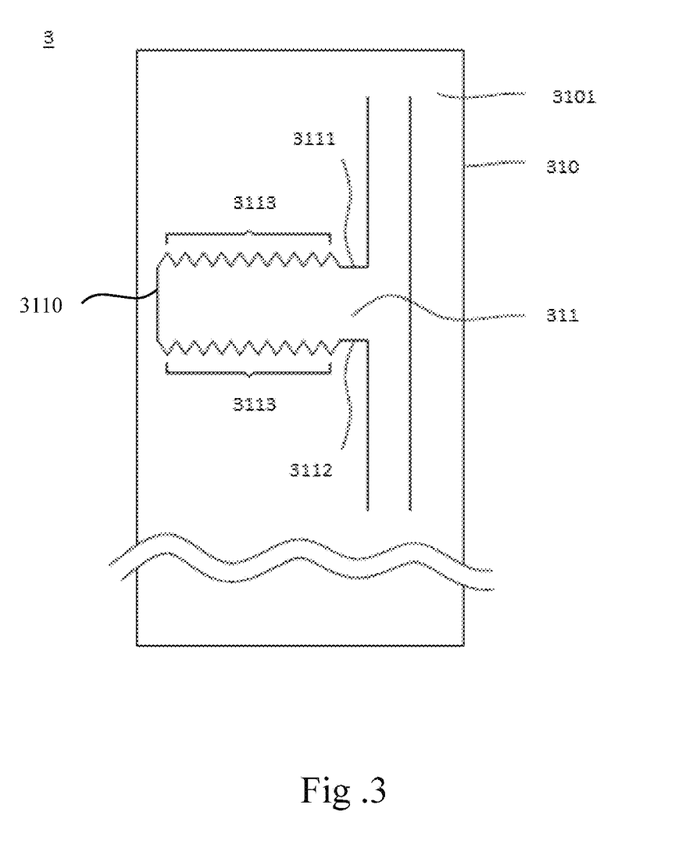
FIG. 3 is a top view of an electrochemical pump according to embodiment 3-1 of the disclosure.

Embodiment 3-1 is similar to the embodiment 1 and 2 and is not repeated in detailed herein, except for the following difference. Please refer to FIG. 3 which is a top cross-sectional view of an electrochemical pump according to embodiment 3 of the disclosure. As shown in FIG. 3, the electrochemical pump 3 comprises a substrate 310 and at least one planar electrode 311.

The planar electrode 311 is disposed on an upper surface 3101 of the substrate 310. Furthermore, in this embodiment, the planar electrode 311 has a first side surface 3111, a second side surface 3112, and a third side surface 3110. A least one sharp corner 3113 can be observed from the top cross-sectional view of the electrochemical pump. The third side surface 3110 of the planar electrode 311 is defined as the surface which connects the first side surface 3111 and the second side surface 3112. The first side surface 3111 is opposite to the second side surface 3112, and both the first side surface 3111 and the second side surface 3112 are connected to the third side surface 3110.

The at least one sharp corner 3113 is formed at and protruded from the first side surface 3111 and/or the second side surface 3112. In a particular embodiment, the sharp corners 3113 of the planar electrode 311 are formed in the shape of zig-zag from the top view of the electrochemical pump 3. Additionally, the planar electrode is porous in this embodiment. However, in an alternative embodiment, the sharp corner is formed on the first side surface 3111, the second side surface 3112, and the third side surface 3110.

In the present invention, the sharp corner can be formed by the techniques known by a skilled person in the art. For example, the sharp corner can be formed via the method of isotropic etching or anisotropic etching.

Figure 4:
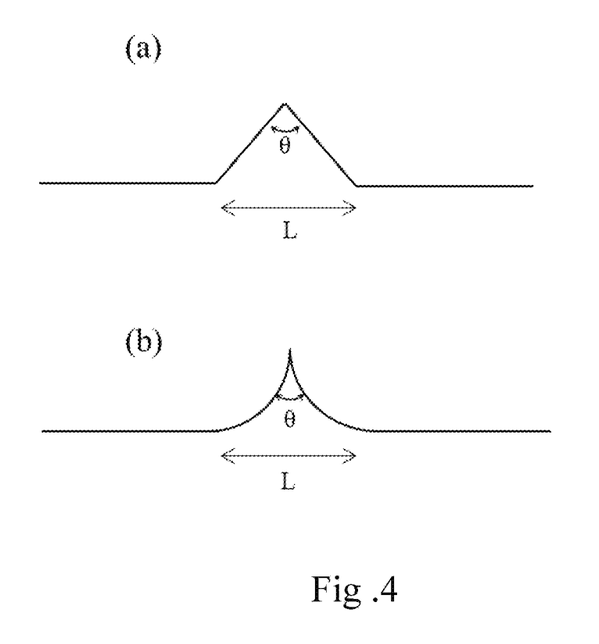
FIG. 4 is an illustrative view of the sharp corner formed on the planar electrode: (a) pyramid-shape; and (b) tip-shape.

However, the shape of the sharp corner can be varied and adjust according to the method of etching. For example, the sharp corner can be pyramid-shaped (FIG. 4(a)) or tip-shaped (FIG. 4(b)). The sharp corner has a sharp angle (θ) which has a range between 0.01-90°. The sharp corner also has a width (L) which has a range between 0.01-100 µm.

Embodiment 3-2

Figure 5:
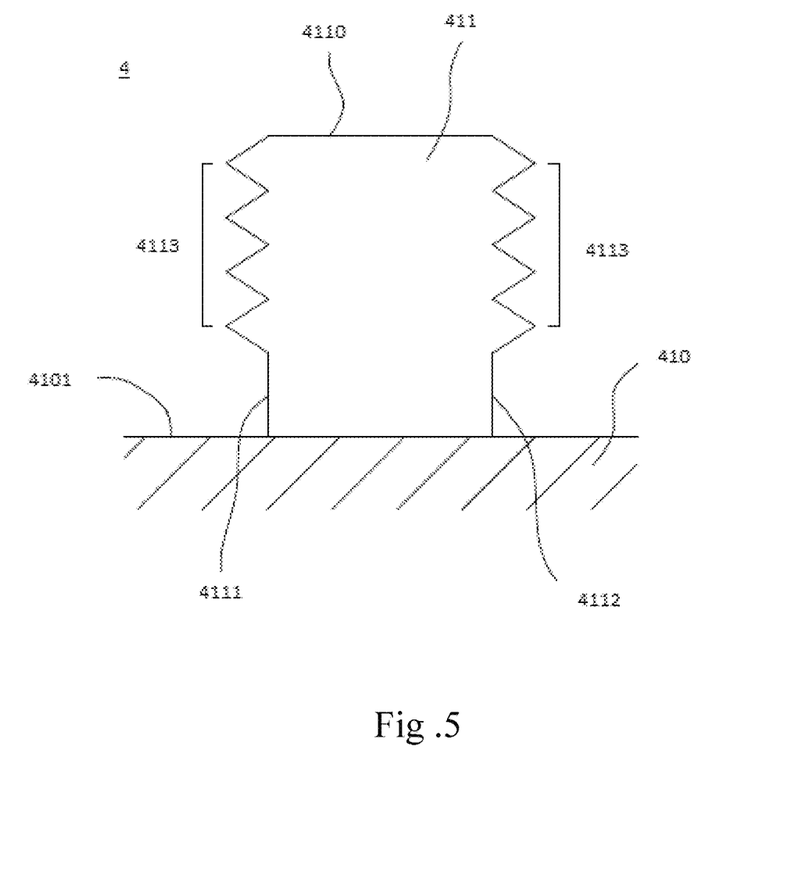
FIG. 5 is a schematic cross-sectional view of an electrochemical pump according to embodiment 3-2 of the disclosure.

Embodiment 3-2 is an alternative view of the embodiment 3-1 and is not repeated in detailed herein. Please refer to FIG. 5, which is a schematic cross-sectional view of an electrochemical pump according to embodiment 3 of the disclosure. As shown in FIG. 5, the electrochemical pump 4 comprises a substrate 410 and at least one planar electrode 411.

The substrate 410 has an upper surface 4101. The planar electrode 411 is disposed on the upper surface 4101 of the substrate 410. Furthermore, in this embodiment, the planar electrode 411 has a top surface 4110, a first side surface 4111, a second side surface 4112 and at least one sharp corner 4113. The top surface 4110 of the planar electrode 411 is substantially parallel to the upper surface 4101 of the substrate 410. The first side surface 4111 is opposite to the second side surface 4112, and both the first side surface 4111 and the second side surface 4112 are connected to the top surface 4110 and substantially perpendicular to the upper surface 4101 of the substrate 410.

Similar to the embodiment shown in FIG. 3, the sharp corners 4113 are formed at and protruded from the first side surface 4111 and the second side surface 4112, and the planar electrode 411 is porous in this embodiment. However, the sharp corners 4113 of the planar electrode 411 are observed in the shape of zig-zag from the side cross-sectional view of the electrochemical pump 4.

Additionally, please refer to FIG. 3 and FIG. 5, in some embodiments (not shown in figures), the planar electrode can be porous, and in a particular embodiment, the number of the sharp corner is more than one.

Embodiment 4

Figure 6:
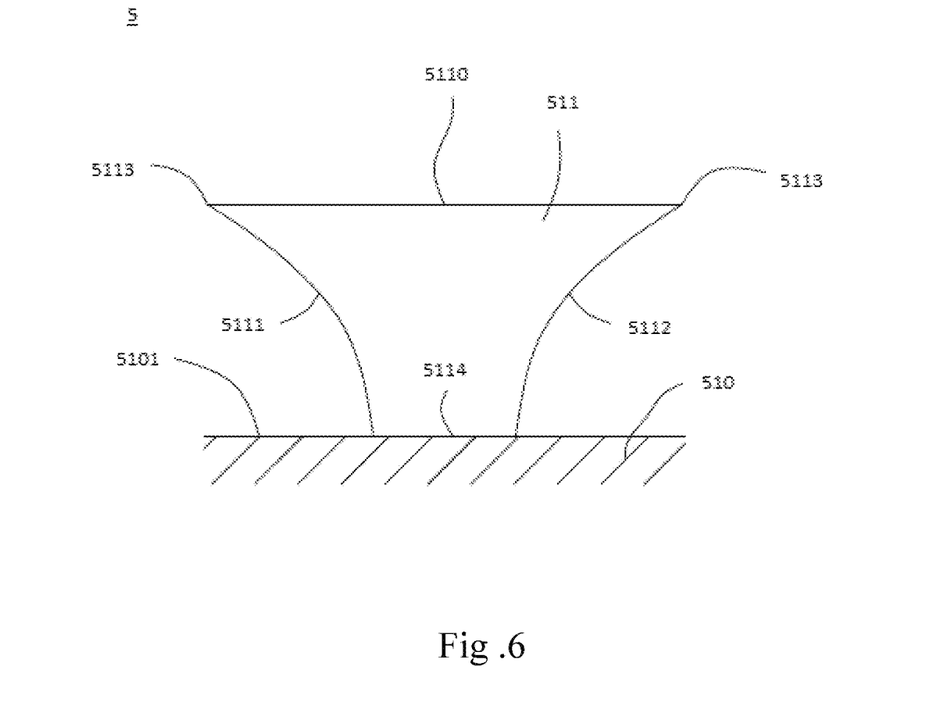
FIG. 6 is a schematic cross-sectional view of an electrochemical pump according to embodiment 4 of the disclosure.

Embodiment 4 is similar to the embodiment 1 and 2 and is not repeated in detailed herein, except for the following difference. Please refer to FIG. 6, which is a schematic cross-section view of an electrochemical pump according to embodiment 4 of the disclosure. As shown in FIG. 6, the electrochemical pump 5 comprises a substrate 510 and at least one planar electrode 511.

The substrate 510 has an upper surface 5101. The planar electrode 511 is disposed on the upper surface 5101 of the substrate 510. Additionally, in this embodiment, the planar electrode 511 has a top surface 5110, a first side surface 5111, a second side surface 5112 and bottom surface 5114. The bottom surface 5114 is opposite to the top surface 5110. The top surface 5110 is substantially parallel to the bottom surface 5114 and the upper surface 5101 of the substrate 510. The first side surface 5111 is opposite to the second side surface 5112, and both the first side surface 5111 and the second side surface 5112 are connected to the top surface 5110 by a sharp corner 5113. In this embodiment, the sharp corner connecting the top surface and the first/second side surface 5111, 5112 has an angle between 0.01 to 90°. Besides, the planar electrode 511 can be porous in this embodiment.

Furthermore, an area of the top surface 5110 is larger than an area of the bottom surface 5114, to form the sharp corners 5113 between the first side surface 5111 and the top surface 5110 and between the second side surface 5111 and the top surface 5110 from the side cross-sectional view.

In some embodiments, the shape of the planar electrode 511 is like an inverse-trapezoid (not shown in figures).

Embodiment 5

Figure 7:
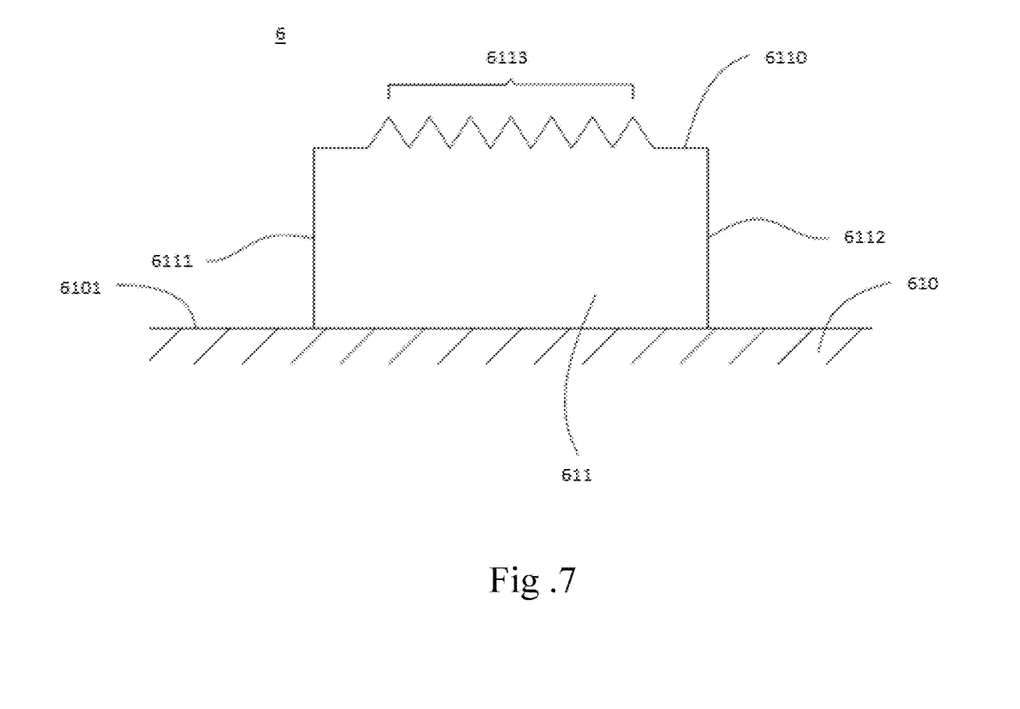
FIG. 7 is a schematic cross-sectional view of an electrochemical pump according to embodiment 5 of the disclosure.

Embodiment 5 is similar to the embodiment 1 and 2 and is not repeated in detailed herein, except for the following difference. Please refer to FIG. 7, which is a schematic cross-sectional view of an electrochemical pump according to embodiment 5 of the disclosure. As shown in FIG. 7, the electrochemical pump 6 comprises a substrate 610 and at least one planar electrode 611.

The substrate 610 has an upper surface 6101. The planar electrode 611 is disposed on the upper surface 6101 of the substrate 610. Furthermore, in this embodiment, the planar electrode 611 has a top surface 6110, a first side surface 6111, a second side surface 6112 and at least one of sharp corner 6113. The top surface 6110 is substantially parallel to the upper surface 6101 of the substrate 610. The first side surface 6111 is opposite to the second side surface 6112, and both the first side surface 6111 and the second side surface 6112 are connected to the top surface 6110.

The sharp corners 6113 are formed at and protruded from the top surface 6110 from the schematic cross-section view. In this embodiment, the shape of each sharp corner 6113 is like pyramid from side cross-sectional view. However, the shape of a sharp corner 6113 is not limited by this embodiment. For example, in some embodiments, the shape of the sharp corners 6113 can be similar to tips (as shown in FIG. 4(b)).

Embodiment 6

Embodiment 6 is similar to the embodiment 1 and 2 and is not repeated in detail herein, except for the following difference. Please refer to FIG. 8, which is a cross-sectional view of a delivery device according to a seventh embodiment of the disclosure.

Figure 8:
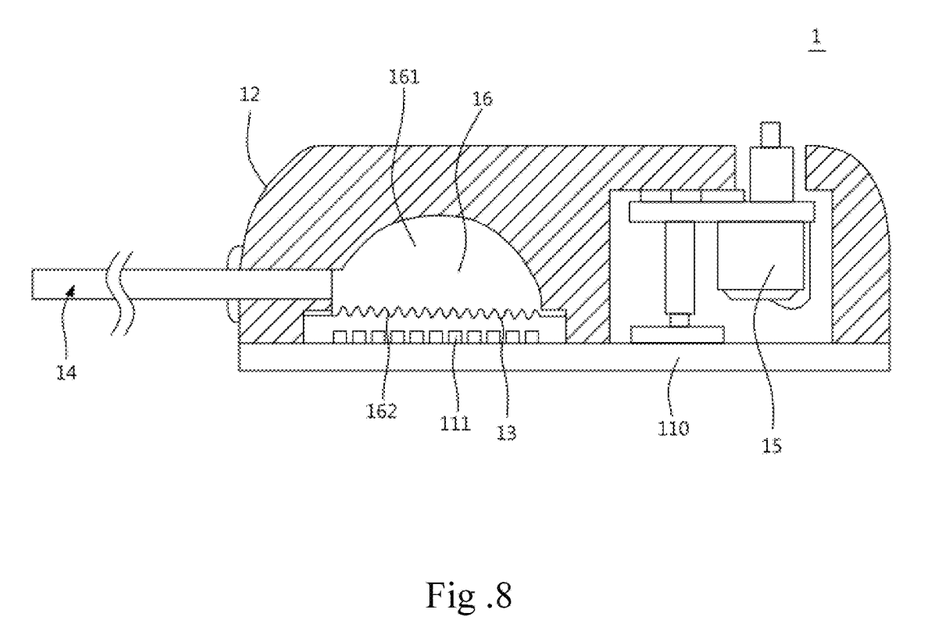
FIG. 8 is a schematic cross-section view of a delivery device according to an alternative embodiment of the disclosure.

The delivery device is vial-shape and the upper surface of the substrate 110 faces an opening in which the cannula 14 is inserted in the embodiment 1. However, the device in the present embodiment has an opening in which the cannula 14 is inserted and the opening does not face the opening. In an embodiment, the opening is in a direction substantially parallel to the substrate 110. Furthermore, the device of the present embodiment also comprises a separator 13 and the separator is made of diaphragm, which is used as a stopper.

Figure 9:
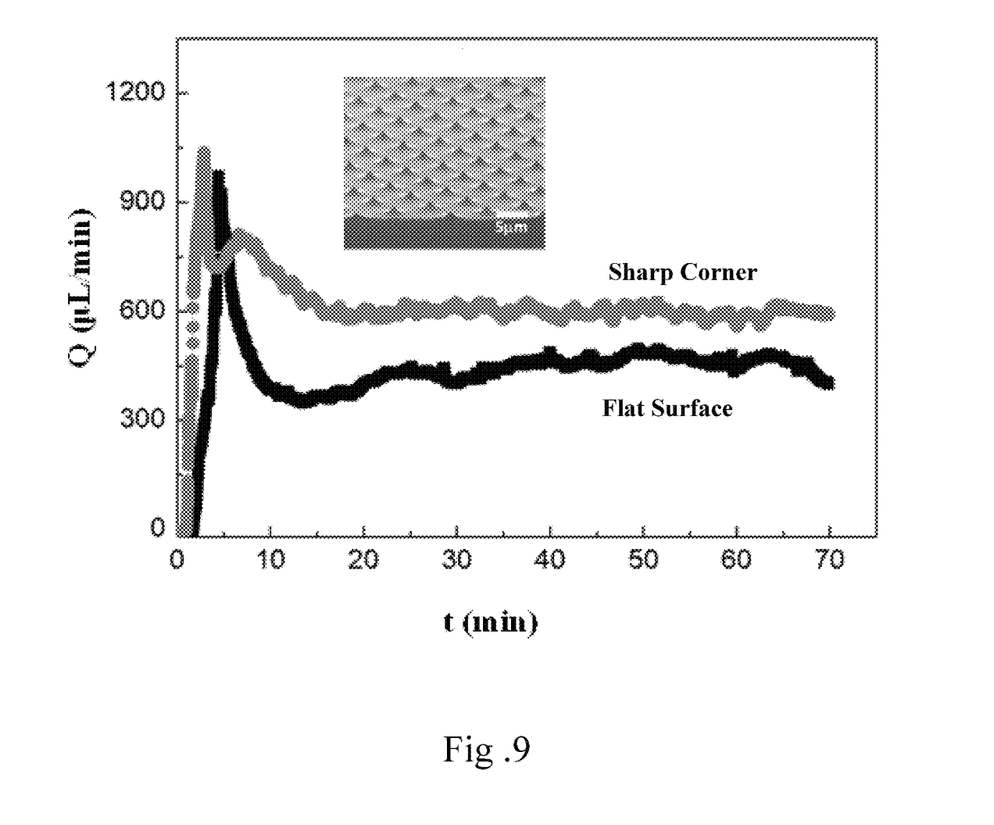
FIG. 9 is a graph showing the flow rate vs. time plot of the micro-delivery device having planar electrode with sharp corner or with flat surface and a figure of the surface of planar electrode under scanning electronic microscope.

According to the present invention, the micro-delivery device which comprises a planar electrode having sharp corner would provide a faster startup speed and a larger amount of fluid compared to the electrode without sharp corner, i.e. compared to the electrode with flat surface. As shown in FIG. 9, the micro-delivery device having a planar electrode with sharp corners provides a faster startup speed for the output of fluid and the amount of fluid is also larger. In contrast, the micro-delivery device having a planar electrode with flat surface provides a slower startup speed for the output of fluid and the amount of fluid is smaller. Hence, it can be observed that the electrode with sharp corner would significantly improve the efficiency of drug delivery of micro-delivery device. FIG. 9 also includes a scanning figure on the surface of the planar electrode by scanning electronic microscope, demonstrating the sharp corners formed on the surface of electrode via etching. As can be observed on the surface of electrode, the sharp corner is distributed on the surface of electrode via etching and the distance between adjacent sharp corners is approximately 5 µm or less.

To be noticed, the structure of the planar electrode is, but not limited to, the shape above-mentioned embodiments shown from FIG. 3 through FIG. 7. For example, please refer to the FIG. 3 and FIG. 7, in some embodiments, the number of the sharp corner is more than one, parts of the sharp corners are formed at and protruded from the side surface in the shape of zig-zag from the top view, and parts of the sharp corners are formed at and protruded from the top surface from the schematic cross-section view.

For example, please refer to FIG. 5 and FIG. 7, in some embodiments, the quantity of the sharp corner is more than one, parts of the sharp corners are formed at and protruded from the side surface in the shape of zig-zag, and parts of the sharp corners are formed at and protruded from the top surface, from schematic cross-section view.

For example, please refer to FIG. 3 and FIG. 6, in some embodiments, the planar electrode is porous, and the quantity of the sharp corner is more than one. Parts of the sharp corners are formed at and protruded from the side surface in the shape of zig-zag from the top view, and parts of the sharp corners are formed between the side surface and the top surface from the schematic cross-section view.

For example, please refer to FIG. 6 and FIG. 7, in some embodiments, the planar electrode is porous, and the quantity of the sharp corner is more than one. Parts of the sharp corners are formed between the side surface and the top surface from the schematic cross-section view, and parts of the sharp corners are formed between the side surface and the top surface from the schematic cross-section view.

For example, please refer to FIG. 5, FIG. 6 and FIG. 7, in some embodiments, the quantity of the sharp corner is more than one, parts of the sharp corners are formed at and protruded from the side surface in the shape of zig-zag from the schematic cross-section view, parts of the sharp corners are formed between the side surface and the top surface from the schematic cross-section view, and parts of the sharp corners are formed at and protruded from the top surface from the schematic cross-section view.

For example, please refer to FIG. 3, FIG. 6 and FIG. 7, in some embodiments, the quantity of the sharp corner is more than one, parts of the sharp corners are formed at and protruded from the side surface in the shape of zig-zag from the top view, parts of the sharp corners are formed between the side surface and the top surface from the schematic cross-section view, and parts of the sharp corners are formed at and protruded from the top surface from the schematic cross-section view.

In some embodiment, for example in FIG. 3, the sharp corner 3113 is formed along a direction substantially perpendicular to the upper surface 3101 of the substrate 310.

In another embodiment, for example in FIG. 5, the sharp corner 4113 is formed along a direction substantially parallel to the upper surface 4101 of the substrate 410.

To sum up, since the electrochemical pump and the delivery device of this disclosure comprise the planar electrode, and the planar electrode comprises the sharp corner, the planar electrode can generate intense electric field and induce larger amount of gas generation (similar to corona discharge in vacuum), for providing better electrolysis efficiency.

While preferred embodiments of the present invention have been shown and described herein, it will be obvious to those skilled in the art that such embodiments are provided by way of example only and can be implemented in combinations. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A micro-delivery device, comprising:
a substrate having an upper surface;
a rigid shell disposed on the upper surface of the substrate and defining a chamber between the rigid shell and the substrate;
a planar electrode disposed on the upper surface of the substrate;
a separator disposed in the chamber and dividing the chamber into an upper reservoir and a lower reservoir; and
a cannula inserted in an opening of the rigid shell and in fluid communication with the upper reservoir,
wherein at least one sharp corner is formed on a surface of the planar electrode, and
wherein the planar electrode has a first side surface and a second side surface which is opposite to the first side surface in a cross-sectional view, and the at least one sharp corner is formed on the first side surface and/or the second side surface respectively.

2. The micro-delivery device as claimed in claim 1, wherein the sharp corner has a width which has a range between 0.01-100 μm.

3. The micro-delivery device as claimed in claim 1, wherein the planar electrode is a porous electrode.

4. The micro-delivery device as claimed in claim 1, further comprising an electronic device is electrically connected to the planar electrode.

5. The micro-delivery device as claimed in claim 1, wherein the planar electrode is hydrophilic and the substrate is hydrophilic.

6. The micro-delivery device as claimed in claim 1, wherein the sharp corners are formed at and protruded from the surface in the shape of zig-zag.

7. A micro-delivery device, comprising:
a substrate having an upper surface;
a rigid shell disposed on the upper surface of the substrate and defining a chamber between the rigid shell and the substrate;
a planar electrode disposed on the upper surface of the substrate;
a separator disposed in the chamber and dividing the chamber into an upper reservoir and a lower reservoir; and
a cannula inserted in an opening of the rigid shell and in fluid communication with the upper reservoir,
wherein at least one sharp corner is formed on a surface of the planar electrode, and
wherein the planar electrode has a first side surface and a second side surface which is opposite to the first side surface in a cross-sectional view, the planar electrode further has a top surface connecting the first side surface and the second side surface, and the at least one sharp corner is formed on the top surface.

8. The micro-delivery device as claimed in claim 1, wherein the sharp corners are formed at and protruded from the surface in the shape of tip of pyramid.

9. The micro-delivery device as claimed in claim 7, wherein the sharp corners are formed at and protruded from the surface in the shape of zig-zag.

10. The micro-delivery device as claimed in claim 7, wherein the sharp corners are formed at and protruded from the surface in the shape of tip of pyramid.

11. The micro-delivery device as claimed in claim 7, wherein the sharp corner has a width which has a range between 0.01-100 μm.

12. The micro-delivery device as claimed in claim 7, wherein the planar electrode is a porous electrode.

13. The micro-delivery device as claimed in claim 7, further comprising an electronic device is electrically connected to the planar electrode.

14. The micro-delivery device as claimed in claim 7, wherein the planar electrode is hydrophilic and the substrate is hydrophilic.

15. A micro-delivery device, comprising:
a substrate having an upper surface;
a rigid shell disposed on the upper surface of the substrate and defining a chamber between the rigid shell and the substrate;
a planar electrode disposed on the upper surface of the substrate;
a separator disposed in the chamber and dividing the chamber into an upper reservoir and a lower reservoir; and
a cannula inserted in an opening of the rigid shell and in fluid communication with the upper reservoir,
wherein at least one sharp corner is formed on a surface of the planar electrode, and
wherein the planar electrode further comprises a top surface and a bottom surface opposite to the top surface, and an area of the top surface is larger than an area of the bottom surface, forming a sharp corner between a side surface and the top surface from a cross-section view.

16. The micro-delivery device as claimed in claim 15, wherein the sharp corner is formed by the method of isotropic etching or anisotropic etching.

17. The micro-delivery device as claimed in claim 15, wherein the sharp corner has a width which has a range between 0.01-100 μm.

18. The micro-delivery device as claimed in claim 15, wherein the planar electrode is a porous electrode.

19. The micro-delivery device as claimed in claim 15, further comprising an electronic device is electrically connected to the planar electrode.

20. The micro-delivery device as claimed in claim 15, wherein the planar electrode is hydrophilic and the substrate is hydrophilic.

\* \* \* \* \*